US00PP29602P3

(12) United States Plant Patent
Suphachadiwong

(10) Patent No.: US PP29,602 P3
(45) Date of Patent: Aug. 14, 2018

(54) ***SANSEVIERIA* PLANT NAMED 'SUPSAN1602'**

(50) Latin Name: *Sansevieria cylindrica*
Varietal Denomination: SUPSAN1602

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/732,332

(22) Filed: Oct. 25, 2017

(65) Prior Publication Data

US 2018/0124987 P1 May 3, 2018

(30) Foreign Application Priority Data

Oct. 31, 2016 (QZ) ..... PBR 2016/2649

(51) Int. Cl.
*A01H 5/12* (2018.01)

(52) U.S. Cl.
USPC ..... Plt./382
CPC ..... *A01H 5/12* (2013.01)

(58) Field of Classification Search
USPC ..... Plt./382
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Sansevieria* plant named 'SUPSAN1602' which is characterized by the combination of a vertically flattened, broad obovate to near orbicular plant form with a slightly spiraling aspect, dark green succulent foliage with subtle light greyed-green radial bands, and the stability of all characteristics from generation to generation.

2 Drawing Sheets

Latin name of the genus and species: The Latin name of the genus and species of the novel variety disclosed herein is *Sansevieria cylindrica.*

Variety denomination:

The inventive variety of *Sansevieria* disclosed herein has been given the variety denomination 'SUPSAN1602'.

CROSS REFERENCE TO RELATED APPLICATIONS

This application claims priority to the Community Plant Variety Rights application number 2016/2649, filed Oct. 31, 2016, which is herein incorporated by reference.

BACKGROUND OF THE INVENTION

Parentage: The *Sansevieria* variety 'SUPSAN1602' originated as a seedling selection from the controlled pollination of the proprietary seed parent, *Sansevieria cylindrica* 'MXU1804' (not patented), with the proprietary pollen parent, *Sansevieria cylindrica* 'MXU1806' (not patented). Both parents were developed by, and are owned by, the inventor and were never commercially released. Said crossing was conducted by the inventor in a small, netted greenhouse in Chonburi, Thailand in November of 2006. Seeds from said cross were harvested, then germinated, and the resulting seedlings were grown to a mature size in order to evaluate for a desirable combination of commercial characteristics. In August of 2008, one candidate plant was observed to exhibit a unique growth habit and leaf coloration. After confirmation of the distinctness and stability of the characteristics first observed, the inventor selected the new *Sansevieria* cultivar, 'SUPSAN1602', for commercial introduction.

Asexual Reproduction: Asexual reproduction of 'SUPSAN1602' by way of harvesting vegetative ground shoots was first initiated in August of 2008 at Chonburi, Thailand. Access to all plants was restricted, as plants were kept in a greenhouse not open to the public. Through subsequent propagation of vegetative ground shoots, five generations have been reproduced which have shown that the unique features of this cultivar are stable and reproduced true to type.

SUMMARY OF THE INVENTION

The cultivar 'SUPSAN1602' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'SUPSAN1602'. These characteristics in combination distinguish 'SUPSAN1602' as a new and distinct *Sansevieria* cultivar:

1. *Sansevieria* 'SUPSAN1602' exhibits an equitant and upright to outward growth habit; and
2. *Sansevieria* 'SUPSAN1602' exhibits a vertically flattened, broad obovate to near orbicular plant form with a slightly spiraling aspect; and
3. *Sansevieria* 'SUPSAN1602' exhibits thick, succulent terete foliage; and
4. *Sansevieria* 'SUPSAN1602' exhibits dark green foliage with subtle light greyed-green radial bands.

BOTANICAL DESCRIPTION OF THE PLANT

Figure 1:
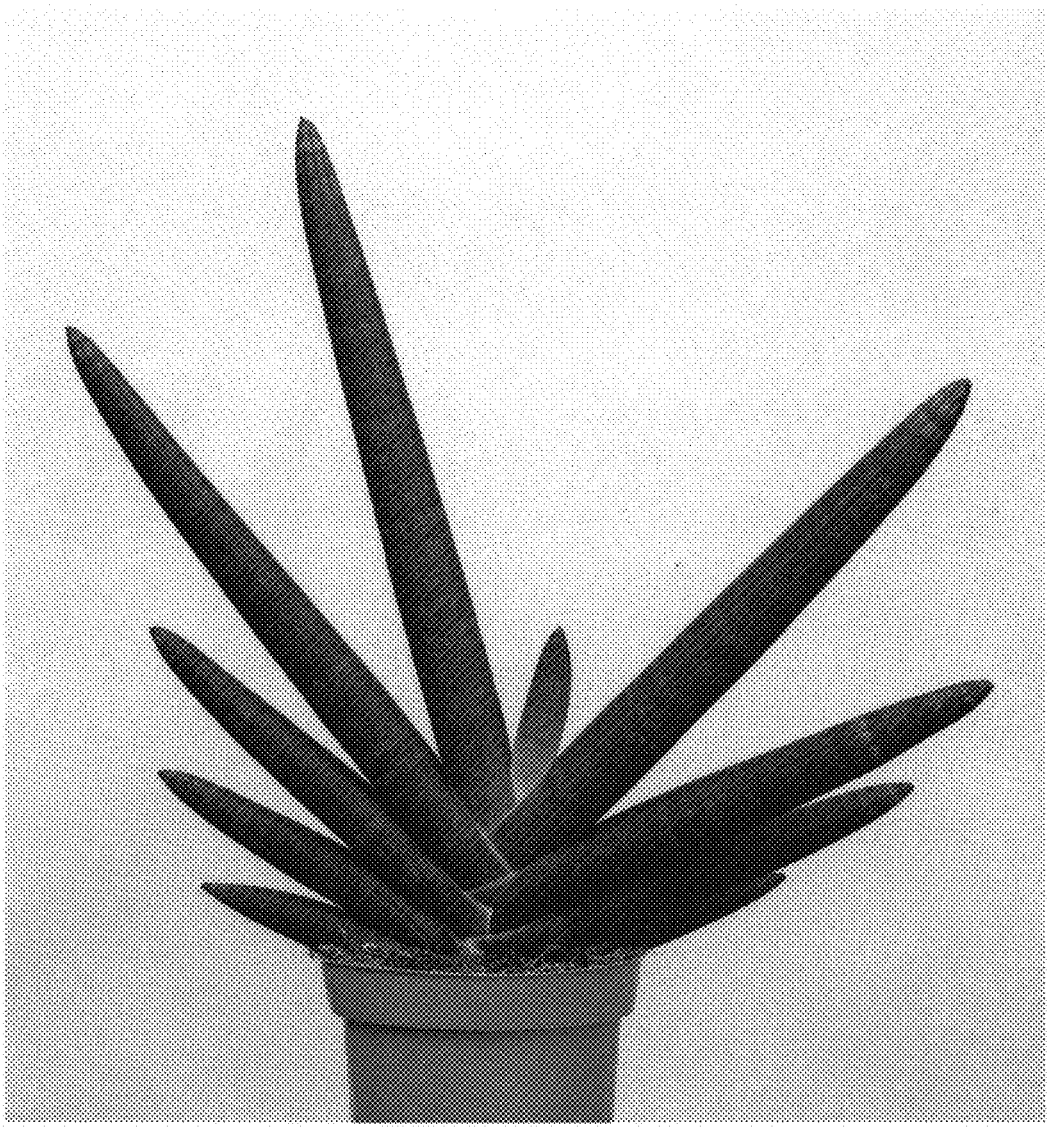
FIG. 1 illustrates, as nearly true as it is reasonably possible to make the same in color photographs of this type, an exemplary plant of 'SUPSAN1602' grown in a commercial greenhouse in Chonburi, Thailand. This plant is approximately 12 months old, shown planted in a 12 cm container.
Figure 2:
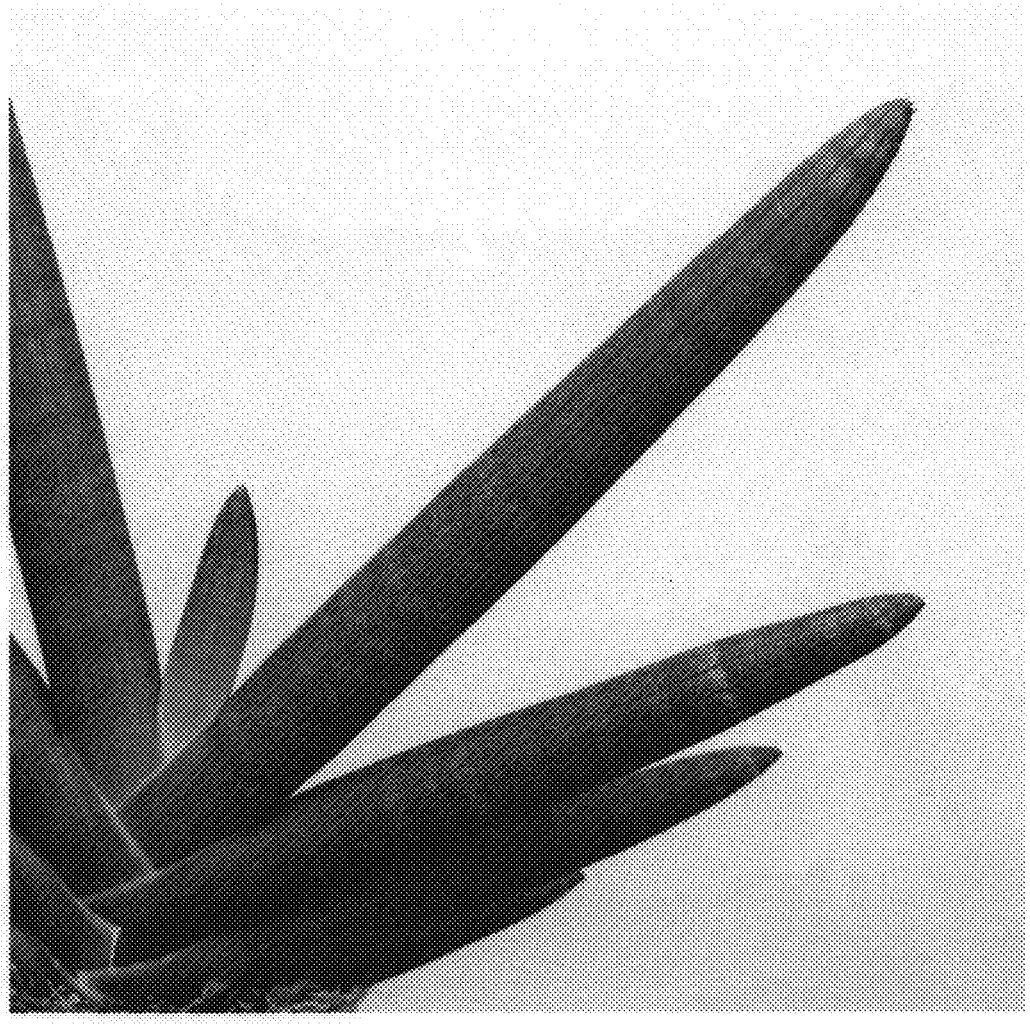
FIG. 2 illustrates, as nearly true as it is reasonably possible to make the same in color photographs of this type, the typical foliage of 'SUPSAN1602'.

The following observations and measurements, made in October of 2017, describe averages from a sample set of six specimens of 12 month old 'SUPSAN1602' plants grown in 12 cm containers, at a commercial greenhouse in Chonburi, Thailand. The plants were grown using conventional greenhouse production protocols for *Sansevieria* plants which consisted of overhead irrigation, 50% shade cloth, and no fertilizer. No photoperiodic or chemical treatments were given to the plants.

Those skilled in the art will appreciate that certain characteristics will vary with older or, conversely, with younger plants. 'SUPSAN1602' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SUPSAN1602' and comparisons with the parents and most similar commercial variety of *Sansevieria* are provided below.

Plant description:

*Growth habit.*—Monopodial perennial; equitant and upright to outward.

*Plant form.*—Vertically flattened with a slightly spiraling aspect; broad obovate to near orbicular at the widest point.

*Average height.*—31.0 cm.

*Plant spread.*—15.8 cm at the narrowest point, and 32.0 cm at the widest point.

*Plant vigor.*—Moderate.

*Growth rate.*—Moderate.

*Propagation type.*—Division of vegetative ground shoots; harvesting ground shoots from the mother plant.

*Propagation details.*—The time needed to root a shoot division is approximately 2 to 3 months with temperatures ranging from approximately 17 to 40 degrees Celsius.

*Disease/pest resistance.*—Plants have not been observed to be susceptible or resistant to pathogens and pests common to *Sansevieria.*

*Environmental tolerances.*—Adapt to, at least, USDA Zones 10 and 12 and temperatures as high as 40 degrees Celsius; moderate tolerance to rain; moderate to high tolerance to wind.

Root system:

*General.*—Moderately dense and moderately branched rooting; roots are slightly fibrous.

*Distribution in the soil profile.*—Shallow to moderately deep.

*Diameter of roots.*—0.15 cm on average.

*Texture.*—Smooth; no root hairs.

*Color.*—Greyed-yellow, nearest to RHS 162D.

Stem:

*Branching habit.*—Monopodial, equitant; decurrent leaf bases form the stem.

*Number of primary (main) stems per plant.*—One.

*Number of secondary (lateral) branches per plant.*—None.

*Appearance and shape.*—Stem is not visible; decurrent leaf bases form the stem.

*Length.*—The decurrent leaf bases collectively have an average length of 5.9 cm.

*Diameter.*—The decurrent leaf bases collectively have an average diameter of 2.8 cm.

*Internode length.*—0.7 cm.

Foliage:

*Arrangement.*—Distichous.

*Attachment.*—Decurrent.

*Division.*—Simple.

*Quantity.*—9.

*Attitude.*—Outward; at an average angle of 50 degrees to vertical.

*Lamina.*—Dimensions — 24.2 cm long and 1.8 cm wide. Thickness — Approximately 2.7 cm. Shape of blade — Linear; succulent. Cross-section — Terete. Aspect — Nearly straight. Apex — Acute with a slightly papery tip which is colored greyed-white, nearest to RHS 156D. Base — Decurrent. Margin — Leaves are terete so there are no margins, with the exception of the leaf base; leaf base margins are entire. Texture of upper surface — Glabrous, smooth, and succulent. Texture of lower surface — Glabrous, smooth, and succulent. Luster of the upper surface — Very slightly glossy. Luster of the lower surface — Very slightly glossy. Color — Juvenile foliage, upper surface — Green, nearest to in between RHS NN137B and NN137C, with mottled radial bands colored greyed-green, nearest to RHS 193A. Juvenile foliage, lower surface — Green, nearest to in between RHS NN137B and NN137C, with mottled radial bands colored greyed-green, nearest to RHS 193A; the base is yellow-green, nearest to in between RHS 144B and 144C. Mature foliage, upper surface — Green, nearest to in between RHS NN137A and 139A, with mottled radial bands colored greyed-green, nearest to RHS 193A. Mature foliage, lower surface — Green, nearest to in between RHS NN137A and 139A, with mottled radial bands colored greyed-green, nearest to RHS 193A; the base is green, nearest to RHS NN137A but slightly darker; margins of the decurrent base are yellow-green, nearest to RHS 148D. Venation — Pattern — Parallel. Color, upper surface — Green, nearest to RHS NN137A. Color, lower surface — Green, nearest to RHS NN137A.

*Petiole.*—No petioles present, leaves are decurrent.

Inflorescence: No flowering has been observed to date.

COMPARISONS WITH THE PARENT PLANTS

Plants of the new cultivar 'SUPSAN1602' differ from the seed parent, *Sansevieria* 'MXU1804' (not patented), by the characteristics described in Table 1.

Comparison Between 'Supsan1602' and 'MXU1804'

TABLE 1

| Characteristic | 'SUPSAN1602' | 'MXU1804' |
|---|---|---|
| Overall plant size. | Smaller than 'MXU1804'. | Larger than 'SUPSAN1602'. |
| Rate of growth. | Slower growing than 'MXU1804'. | Faster growing than 'SUPSAN1602'. |
| Leaf thickness. | Thicker than 'MXU1804'. | Thinner than 'SUPSAN1602'. |
| Leaf length. | Shorter than 'MXU1804'. | Longer than 'SUPSAN1602'. |
| General coloration of the foliage. | Lighter green. | Darker green. |
| Leaf pattern. | Lesser occurrence of greyed-green mottled radial bands. | Greater occurrence of greyed-green mottled radial bands. |

Plants of the new cultivar 'SUPSAN1602' differ from the pollen parent, *Sansevieria* 'MXU1806' (not patented), by the characteristics described in Table 2.

Comparison Between 'Supsan1602' and 'MXU1806'

TABLE 2

| Characteristic | 'SUPSAN1602' | 'MXU1806' |
|---|---|---|
| Overall plant size. | Larger than 'MXU1806'. | Smaller than 'SUPSAN1602'. |
| Rate of growth. | Faster growing than 'MXU1806'. | Slower growing than 'SUPSAN1602'. |
| Leaf thickness. | Thinner than 'MXU1806'. | Thicker than 'SUPSAN1602'. |

TABLE 2-continued

| Characteristic | 'SUPSAN1602' | 'MXU1806' |
|---|---|---|
| Leaf length. | Longer than 'MXU1806'. | Shorter than 'SUPSAN1602'. |
| General coloration of the foliage. | Darker green. | Lighter green. |

COMPARISON WITH THE MOST SIMILAR *SANSEVIERIA* CULTIVAR KNOWN TO THE INVENTOR

Plants of the new cultivar 'SUPSAN1602' are most similar to the commercial cultivar, *Sansevieria cylindrica* 'SAN201202' (U.S. Plant Pat. No. 24,457). A comparison of 'SUPSAN1602' with 'SAN201202' is described in Table 3.

Comparison Between 'Supsan1603' and 'San201202'

TABLE 3

| Characteristic | 'SUPSAN1602' | 'SAN201202' |
|---|---|---|
| Leaf attitude. | More outward. | More upright. |
| Leaf thickness. | Thinner than 'SAN201202'. | Thicker than 'SUPSAN1602'. |
| General coloration of the foliage. | Dark green. | Light greyed-green. |
| Leaf pattern. | Subtle mottled radial bands. | Prominent mottled radial bands. |

That which is claimed is:

1. A new and distinct variety of *Sansevieria* plant named 'SUPSAN1602', substantially as described and illustrated herein.

* * * * *